US009211424B2

(12) United States Patent
Nguyen et al.

(10) Patent No.: US 9,211,424 B2
(45) Date of Patent: *Dec. 15, 2015

(54) USE OF A NON-HYDROXIDE BASE WITH HEAT FOR RELAXING OR STRAIGHTENING HAIR

(75) Inventors: Nghi Van Nguyen, Edison, NJ (US); David W. Cannell, New Hope, PA (US); Cynthia Chong Espino, Princeton, NJ (US); Sawa Hashimoto, Westfield, NJ (US)

(73) Assignee: L'OREAL (FR)

( * ) Notice: Subject to any disclaimer, the term of this patent is extended or adjusted under 35 U.S.C. 154(b) by 0 days.

This patent is subject to a terminal disclaimer.

(21) Appl. No.: 13/367,899

(22) Filed: Feb. 7, 2012

(65) Prior Publication Data

US 2012/0132224 A1 May 31, 2012

Related U.S. Application Data

(63) Continuation of application No. 11/446,718, filed on Jun. 5, 2006, now Pat. No. 8,603,448.

(51) Int. Cl.
| | |
|---|---|
| *A61Q 5/04* | (2006.01) |
| *A45D 7/02* | (2006.01) |
| *A61K 8/19* | (2006.01) |
| *A61K 8/24* | (2006.01) |
| *A61K 8/41* | (2006.01) |

(52) U.S. Cl.
CPC ... *A61Q 5/04* (2013.01); *A61K 8/19* (2013.01); *A61K 8/24* (2013.01); *A61K 8/41* (2013.01)

(58) Field of Classification Search
None
See application file for complete search history.

(56) References Cited

U.S. PATENT DOCUMENTS

| | | | |
|---|---|---|---|
| 2,437,965 A | | 3/1948 | Michaels et al. |
| 2,770,599 A | | 11/1956 | Henkin |
| 3,457,027 A | | 7/1969 | Bolinger et al. |
| 3,973,574 A | | 8/1976 | Minagawa et al. |
| 4,192,863 A | | 3/1980 | Kondo |
| 4,228,810 A | | 10/1980 | Moore et al. |
| 4,296,764 A | | 10/1981 | Pallone et al. |
| 4,524,787 A | | 6/1985 | Khalil et al. |
| 4,793,994 A | | 12/1988 | Helioff et al. |
| 4,847,076 A | | 7/1989 | Deshpande et al. |
| 4,898,726 A | | 2/1990 | Beste |
| 5,293,885 A | | 3/1994 | Darkwa et al. |
| 5,520,209 A | * | 5/1996 | Goins et al. ............... 137/246 |
| 5,520,909 A | | 5/1996 | Salce et al. |
| 5,565,216 A | | 10/1996 | Cowsar et al. |
| 5,776,443 A | | 7/1998 | Vinski et al. |
| 5,833,966 A | | 11/1998 | Samain |
| 5,854,319 A | | 12/1998 | O'Lenick, Jr. et al. |
| 6,491,902 B2 | | 12/2002 | Shefer et al. |
| 6,706,674 B2 | | 3/2004 | Cincotta et al. |
| 6,805,136 B2 | | 10/2004 | Browning |
| 7,115,253 B1 | | 10/2006 | Zucchetti et al. |
| 7,638,117 B2 | | 12/2009 | Shami |
| 2001/0023235 A1 | | 9/2001 | Crudele et al. |
| 2002/0110583 A1 | | 8/2002 | Grey |
| 2002/0146379 A1 | | 10/2002 | Shefer et al. |
| 2002/0155962 A1 | | 10/2002 | Cincotta et al. |
| 2004/0034946 A1 | | 2/2004 | Legrand et al. |
| 2004/0122105 A1 | | 6/2004 | Bettle et al. |
| 2004/0146476 A1 | | 7/2004 | Shami |
| 2005/0048018 A1 | | 3/2005 | Fadeeva et al. |
| 2005/0125914 A1 | | 6/2005 | Malle et al. |
| 2005/0136016 A1 | * | 6/2005 | Malle et al. ............... 424/70.2 |
| 2005/0136017 A1 | * | 6/2005 | Malle et al. ............... 424/70.2 |
| 2005/0136018 A1 | * | 6/2005 | Malle et al. ............... 424/70.2 |
| 2005/0186232 A1 | * | 8/2005 | Malle et al. ............... 424/401 |
| 2006/0127337 A1 | | 6/2006 | Radisson |
| 2006/0228316 A1 | | 10/2006 | Cannell et al. |
| 2006/0251599 A1 | | 11/2006 | Savaides et al. |
| 2007/0218027 A1 | | 9/2007 | Nguyen et al. |
| 2007/0280895 A1 | | 12/2007 | Weimer et al. |
| 2007/0280896 A1 | | 12/2007 | Nguyen et al. |
| 2008/0223392 A1 | | 9/2008 | Cannell et al. |
| 2011/0052520 A1 | | 3/2011 | Nguyen et al. |
| 2012/0132224 A1 | | 5/2012 | Nguyen et al. |

FOREIGN PATENT DOCUMENTS

| | | | |
|---|---|---|---|
| DE | 19855606 A1 | | 6/2000 |
| EP | 0167866 | | 1/1986 |
| EP | 0640643 A2 | | 3/1995 |
| EP | 0868900 | | 10/1998 |
| EP | 1532963 | * | 5/2005 |
| EP | 1532963 A1 | | 5/2005 |
| EP | 1532964 | * | 5/2005 |
| EP | 1532964 A1 | | 5/2005 |
| EP | 1535607 | | 6/2005 |
| EP | 1752130 | | 2/2007 |
| EP | 1880707 | | 1/2008 |
| FR | 2862213 | * | 1/2004 |
| FR | 2862212 | * | 5/2005 |
| GB | 1416565 A | | 12/1975 |
| GB | 1545297 A | | 5/1979 |

(Continued)

OTHER PUBLICATIONS

Japanese Straightening FAQ. http://straightening.blogspot.com/2005_05_01 archive.html Accessed Apr. 13, 2010.

(Continued)

*Primary Examiner* — Jyothsna Venkat
(74) *Attorney, Agent, or Firm* — Lerner, David, Littenberg, Krumholz & Mentlik, LLP

(57) ABSTRACT

A process for straightening or relaxing hair involving the steps of: (a) providing a hair straightening/relaxing composition containing: (i) from about 0.1 to about 50% by weight of at least one weak non-hydroxide base; and (ii) remainder, to 100%, a cosmetically acceptable medium, all weights based on the weight of the hair straightening/relaxing composition; (b) contacting the hair with the hair straightening/relaxing composition to form treated hair; (c) optionally, rinsing the hair straightening/relaxing composition from the treated hair; (d) optionally, contacting the treated hair with a non-volatile oil; and (e) smoothing the treated hair using a combination of heat and means for physically smoothing hair.

22 Claims, No Drawings

(56) References Cited

FOREIGN PATENT DOCUMENTS

| GB | 1600807 A | 10/1981 |
|---|---|---|
| JP | H03251519 A | 11/1991 |
| JP | H05331029 A | 12/1993 |
| JP | H06192051 A | 7/1994 |
| JP | H09132515 A | 5/1997 |
| JP | 2000016923 | 1/2000 |
| JP | 2000256146 A | 9/2000 |
| JP | 2000302647 A | 10/2000 |
| JP | 2001247436 | 9/2001 |
| JP | 2002138022 A | 5/2002 |
| JP | 2002308725 A | 10/2002 |
| JP | 2003171238 A | 6/2003 |
| JP | 2004026770 A | 1/2004 |
| JP | 2008222717 A | 9/2008 |
| WO | 8800186 A1 | 1/1988 |
| WO | 02085317 A1 | 10/2002 |
| WO | 2004069214 A1 | 8/2004 |
| WO | 2009117344 A2 | 9/2009 |

OTHER PUBLICATIONS

Office Action from Chinese Application No. 200780020658.7, dated Jun. 10, 2010.
Office Action from Chinese Application No. 200780020658.7, dated Mar. 2, 2011.
Yu Zhiming et al., Encyclopedia of Chinese Chemical Commodities 1995 Edition, vol. 1, China Logistics Publishing House, Jan. 1996, p. 359 and 363.
Chinese Office Action for Application No. 200780020658.7 dated Sep. 29, 2013.
Flat Ironing Creme. http://web.archive.org/web/20060103033615/http://www.growafrohairlong.com/flatironing.html, Accessed Apr. 14, 2010, Archived Jan. 3, 2006.
Glossary of Cosmetics Terms. http://www.salonweb.com/pro/glossary.htm. Published Nov. 8, 2001.
Golczewski. Exp Gerontal. 1984; 19(1): Abstract only.
How Long Do You Process. http://www.longhaircareforum.com/showthread.php?t=91703. Published Jun. 29, 2006.
International Preliminary Report on Patentability dated Dec. 10, 2008 in corresponding PCT application No. PCT/US07/09645.
International Preliminary Report on Patentability dated Sep. 30, 2010 as received in corresponding PCT application No. PCT/US2009/037245.
International Search Report and Written Opinion dated Apr. 20, 2009 as received in corresponding PCT application No. PCT/US2009/037245.
International Search Report and Written Opinion of the International Searching Authority dated Aug. 11, 2008 in corresponding PCT application No. PCT/US07/09645.
International Search Report for Application PCTUS07/09645 dated Aug. 11, 2008.
Jerry March, Advanced Organic Chemistry, Reactions, Mechanisms, and Structure, Third Edition, p. 218 to 223, A Wiley-Interscience Publication, John Wiley&Sons, New York, Chichester, Brisbane, Toronto, Singapore, Copyright 1985.
Milady's Standard Cosmetology. Copyright 2004. Milady.
Perm Can Hurt or Help. http://www.naturallycurly.com/curlreading/straightening/perm-can-hurt-or-help. Accessed Apr. 13, 2010.
Production Chemicals for the Oil and Gas Industry. Copyright 2009. Malcom A Kelland.
Solano Professional Flat Iron as accessed from http://www.healthstore.com/hairtools.html on Apr. 6, 2009 as archived Jun. 2, 2002.
Extended European Search Report for Application No. 07775837.3 dated Dec. 9, 2014.
Extended European Search Report for Application No. EP 08300129 dated Aug. 8, 2014.
Extended European Search Report for Application No. EP09721486 dated Mar. 26, 2015.

* cited by examiner

USE OF A NON-HYDROXIDE BASE WITH HEAT FOR RELAXING OR STRAIGHTENING HAIR

CROSS-REFERENCE TO RELATED APPLICATIONS

The present application is a continuation of U.S. patent application Ser. No. 11/446,718, filed on Jun. 5, 2006, the disclosure of which is incorporated herein by reference.

BACKGROUND OF THE INVENTION

Hair straightening or hair relaxing products have been commercially available for over fifty years for people who want straighter, more manageable hair. Most commercially available hair relaxers are composed of a strong hydroxide base that breaks the bonds in the hair.

Commercial products based only on alkaline metal hydroxides such as sodium hydroxide and lithium hydroxide are typically used to straighten or relax curly/kinky hair. There are primarily four different types of alkaline metal hydroxide hair straighteners in use: calcium hydroxide, lithium hydroxide, sodium hydroxide, and potassium hydroxide. The straightening product is usually applied quickly and can only remain in the hair for a very limited amount of time. Due to the alkalinity of such products, if the product is not rinsed from the hair at the appropriate time, damage to the hair can occur, as well as chemical burns to the scalp and areas surrounding the hair.

Thus, the object of the present invention is to provide a hair straightening or relaxing process which is safer than, yet as effective as, conventional processes.

BRIEF SUMMARY OF THE INVENTION

The present invention is directed to a process for straightening or relaxing hair involving the steps of:
(a) providing a hair straightening/relaxing composition containing:
(i) from about 0.1% to about 50% by weight of at least one weak non-hydroxide base; and
(ii) remainder, to 100%, of a cosmetically acceptable medium;
(b) contacting the hair with the hair straightening/relaxing composition to form treated hair;
(c) optionally, rinsing the hair straightening/relaxing composition from the treated hair;
(d) optionally, contacting the treated hair with a non-volatile oil; and
(e) smoothing the treated hair using a combination of heat and means for physically smoothing hair.

DETAILED DESCRIPTION OF THE INVENTION

Other than in the operating examples, or where otherwise indicated, all numbers expressing quantities of ingredients and/or reaction conditions, are to be understood as being modified in all instances by the term "about".

The present invention is directed to a process for straightening or relaxing hair using: (a) a straightening/relaxing composition containing: (i) at least one non-hydroxide weak base and (ii) a cosmetically acceptable medium, and (b) means for physically smoothing hair.

It has been surprisingly found that by employing the process of the present invention, straightening/relaxing of the hair can be achieved in a manner which is safe for the user's skin, as well as their hair. This is due to the present invention's use of a weak non-hydroxide base in the straightening/relaxing process.

Conventional products, which employ large amounts of hydroxide, have a tendency to cause both skin irritation, as well as damage to the hair, due to the use of large amounts of hydroxide in said products. However, by employing a weak non-hydroxide base product, in combination with heat and means for physically smoothing the hair, satisfactory straightening/relaxing of the hair can be achieved in a manner that is safe for both skin and hair.

Suitable weak non-hydroxide bases for use in the present invention are those bases having a pKa of from about 0 to about 15, preferably from about 1 to about 14, and more preferably from about 2 to about 13. These may be chosen from weak organic bases and weak inorganic bases.

Weak organic bases generally include nitrogen-containing bases which do not completely disassociate in water. Examples thereof include, but are not limited to, ethylamines, ethyleneamines, ethanolamines, quinoline, aniline, pyridine, and their derivatives.

Particularly preferred weak organic bases include ethylenediamines and monoethanolamines.

Weak inorganic bases generally include alkali metal phosphates and carbonates such as, for example, sodium phosphate, potassium phosphate, sodium carbonate, sodium bicarbonate, potassium carbonate, potassium bicarbonate, and their derivatives.

Weak inorganic bases may also include alkali metals of carboxylates such as, for example, sodium acetate, potassium acetate, sodium citrate, and potassium citrate, and their derivatives.

Particularly preferred weak inorganic bases include potassium phosphate, sodium phosphate, and sodium carbonate.

The weak non-hydroxide base is typically employed in the hair straightening/relaxing composition in an amount of from about 0.1% to about 50% by weight, preferably from about 0.1% to about 30% by weight, preferably from about 0.1% to about 10% by weight, based on the total weight of the composition.

As used herein, the term "cosmetically acceptable medium" is known to one of ordinary skill in the art, and may comprise, for example, water and/or at least one organic solvent.

The hair straightening/relaxing composition disclosed herein may be, for example, in the form of a thickened cream so as to hold the hair as stiff as possible. These creams are made in the form of "heavy" emulsions, for example, based on glyceryl stearate, glycol stearate, self-emulsifying waxes, fatty alcohols, mineral oil and petrolatum.

Liquids or gels containing thickeners, such as carboxyvinyl polymers or copolymers that "stick" the hairs together and hold them in a smooth position during the leave-in time, may also be used.

The hair straightening/relaxing composition as disclosed herein may also comprise at least one adjuvant chosen, for example, from silicones in soluble, dispersed and microdispersed forms, nonionic, anionic, cationic and amphoteric surfactants, ceramides, glycoceramides and pseudoceramides, vitamins and provitamins including panthenol, waxes other than ceramides, glycoceramides and pseudoceramides, water-soluble and liposoluble, silicone-based and non-silicone-based sunscreens, nacreous agents and opacifiers, sequestering agents, plasticizers, solubilizers, acidifying agents, mineral and organic thickeners, antioxidants, hydroxy acids, penetrating agents, fragrances, and preserving agents.

In the event that surfactants are employed in the composition of the present invention, said composition may be used as a shampoo. Similarly, in the event that one were to decide to use the composition of the invention as a hair conditioner, various types of conditioning agents can be added to the composition in order to facilitate this hair treating property.

Smoothing of hair treated with the above-disclosed hair straightening/relaxing composition involves using a combination of heat and means for physically smoothing the hair. The heat necessary to effectuate smoothing should be at least 50° C.; preferably at least 75° C.; preferably at least 100° C. The precise amount of heat employed will depend on the concentration of the non-hydroxide compound present in the composition. This heat may emanate from any suitable source such as, for example, a hair dryer or hot/flat iron.

The means for physically smoothing hair can be any apparatus capable of physically smoothing the hair such as, for example, a hair brush or comb. In one embodiment, the means for smoothing hair also serves as the source for generating heat such as, for example, a hot/flat iron.

According to one embodiment of the present invention, there is provided a process for straightening or relaxing hair involving the steps of: (a) contacting the hair with the above-disclosed hair straightening/relaxing composition to form treated hair; (b) optionally, rinsing the hair straightening/relaxing composition from the treated hair, after it has been in contact with the hair for a period of less than 60 minutes, preferably less than 40 minutes, preferably less than 30 minutes, preferably less than 20 minutes; (c) optionally, contacting the treated hair with a non-volatile oil chosen from plant, animal, mineral and synthetic oils; and (d) smoothing the treated hair using a combination of heat and means for physically smoothing hair.

As is disclosed above, the hair straightening/relaxing composition may either be left on the hair, or rinsed out. As for the non-volatile oil, if employed, it will preferably remain on the hair.

According to another embodiment of the present invention, there is provided a process for straightening or relaxing hair involving the steps of: (a) optionally, contacting the hair with a non-volatile oil chosen from plant, animal, mineral and synthetic oils; (b) smoothing the treated hair using a combination of heat and means for physically smoothing hair to form smoothed hair; (c) contacting the smoothed hair with the hair straightening/relaxing composition to form treated hair; (d) optionally, rinsing the hair straightening/relaxing composition from the treated hair after it has been in contact with the hair for a period of less than 60 minutes, preferably less than 40 minutes, preferably less than 30 minutes, preferably less than 20 minutes; and (e) optionally, smoothing the treated hair using a combination of heat and means for physically smoothing hair to form smoothed hair.

It should be noted that the steps of: contacting the hair with a non-volatile oil; and smoothing the hair, may be performed prior to and/or after application of the hair straightening/relaxing composition.

In commercially available hair straightening or relaxing compositions, the highly caustic hydroxide compound such as sodium hydroxide must be used in order to satisfactorily straighten/relax the hair without heat. In the present invention, however, the less caustic and the lower concentrations of the non-hydroxide compound can be used because of the synergy realized by using a combination of heat and an apparatus capable of physically smoothing the hair. Without intending to be bound by theory, it is believed that a synergistic effect in hair straightening/relaxing is realized due to an induced supercontraction and denaturation of hair protein caused by the combination of heat and physical smoothing.

Moreover, due to the less caustic and the lower concentrations of the non-hydroxide compound being used, a barrier substance is not required when using the hair straightening/relaxing composition of the present invention. Commercially available hair relaxing products oftentimes require the hair stylist to apply a barrier substance such as petrolatum to the skin surrounding the scalp and the area around the ears. The barrier substance is used to prevent the skin from becoming irritated if the hair relaxing product contacts the skin. A barrier substance is not necessary when using the process of the present invention because the concentration and the irritation of the non-hydroxide compound is much lower.

The present invention will be better understood from the examples which follow, all of which are intended for illustrative purposes only, and are not meant to unduly limit the scope of the invention in any way.

EXAMPLES

General Procedure to Test the Straightening Efficiency of the Kinky Hair:

The tests were done on hair swatches made of 45 strands of kinky hair, 10 cm long (full length when straight). The following treatments were performed:

Leave-on: The hair swatches were soaked in various base solutions for the indicated amount of time then blotted dry once with paper towel.

Rinse-out: The hair swatches were soaked in the various base solutions for the indicated amount of time then rinsed with water for 5 seconds and blotted dry once with paper towel.

Heat: The hair was then straightened by passing the flat iron at 193° C. over the hair three times, 6-7 seconds each pass.

After the treatments, as defined as above, the straightened hair swatches were shampooed with 15% SLES-2 (pH=6.0) solution three times (5 seconds of shampooing and 5 seconds of rinsing each time). The final length of the hair was measured when the hair was completely dry at ambient condition.

The Percentage Straightening Efficiency (% SE) was calculated using the following formula:

% SE=(A/B)×100, where A=final length measured (cm), B=initial length of hair (10 cm)(full length of hair when straight).

The following examples show the % SE of hair treated with various protocols.

Example 1

Treat—Leave-on—Heat Protocol

The kinky hair was treated with 0.1%, 0.5%, 1%, 2%, 4%, 8% solutions of Potassium Phosphate, Sodium Phosphate, Ethylenediamine, and Monoethanolamine for 20 minutes as leave-on treatments then flat ironed. The % SE are shown below.

|  | 0.1% | 0.5% | 1% | 2% | 4% | 8% |
| --- | --- | --- | --- | --- | --- | --- |
| $K_3PO_4$ | 36% | 55% | 61% | 69% | 98.5% | 100% |
| $Na_3PO_4$ | 31.5% | 32% | 59.5% | 71% | 86.5% | 100% |
| Ethylenediamine | 29% | 69% | 79% | 90% | 94.5% | 86.5% |
| MEA | 27.5% | 45% | 65.5% | 85.5% | 93% | 99.5% |

The control swatches, which were soaked in the 8% solutions of $K_3PO_4$, $Na_3PO_4$, Ethylenediamine, and MEA for 20 minutes as leave-on without ironing, had the % SE of 37%, 35%, 36%, and 28%, respectively.

The results show that in the Treat—Leave-on—Heat protocol, kinky hair was effectively straightened by the use of the bases coupled with the heat. Also, the % SE increased with the increase in the concentration.

Example 2

Treat—Rinse-Out—Heat Protocol

The kinky hair was treated with 1%, 4%, 7%, 10%, 13% solutions of Sodium Phosphate, Ethylenediamine, and Monoethanolamine for 30 minutes as rinse-out treatments then flat ironed. The control swatches were also soaked in the above solutions for 30 minutes as rinse-out without ironing. The % SE are shown below.

|  | 1% | 4% | 7% | 10% | 13% |
|---|---|---|---|---|---|
| $Na_3PO_4$ with Heat | 32% | 90% | 92% | 96.50% | 100% |
| $Na_3PO_4$ without Heat | 29% | 28% | 32% | 43% | 42% |
| Ethylenediamine with Heat | 86% | 86.50% | 90% | 90% | 92.50% |
| Ethylenediamine without Heat | 27% | 27% | 35% | 29% | 25% |
| MEA with Heat | 55% | 70.50% | 83.50% | 87.50% | 90% |
| MEA without Heat | 23% | 27% | 30% | 30% | 23% |

The results show that in the Treat—Rinse-out—Heat protocol, kinky hair was effectively straightened by the use of the bases coupled with the heat. Also, the % SE increased with the increase in the concentration.

Example 3

Heat—Treat—Rinse-Out—Heat Protocol

The curly hair was straightened with the flat iron then treated with 0.75% solution of Ethylenediamine for 30 minutes as a rinse-out treatment then flat ironed. As for the controls, the hair was treated following the same protocol but without the heat treatment. The % SE was calculated after the hair swatches were shampooed 3 times, soaked in water for 1 hour and air dried.
The % SE are shown below.

| Protocol | % SE |
|---|---|
| Heat - Treat - Rinse-out | 48% |
| Treat - Rinse-out - Heat | 61.50% |
| Heat - Treat - Rinse-out - Heat | 84.50% |

The results show that smoothing and straightening the hair with heat prior to the rinse-out treatment improves the straightening efficiency.

Example 4

Heat—Treat—Leave-on—Heat Protocol

The curly hair was straightened with the flat iron then treated with 0.75% solution of Ethylenediamine for 30 minutes as a leave-on treatment then flat ironed. As for the controls, the hair was treated following the same protocol but without the heat treatment. The % SE was calculated after the hair swatches were shampooed 3 times, soaked in water for 1 hour and air dried.
The % SE are shown below.

| Protocol | % SE |
|---|---|
| Heat - Treat - Leave-on | 42.50% |
| Treat - Leave-on - Heat | 71% |
| Heat - Treat - Leave-on - Heat | 84.00% |

The results show that smoothing and straightening the hair with heat prior to the leave-on treatment improves the straightening efficiency.

As can be seen from the above data, the use of a hot iron as the means of smoothing/straightening the hair significantly increased the degree of straightening achieved by the hair straightening/relaxing composition of the present invention.

What is claimed is:
1. A process for straightening or relaxing hair comprising:
   (a) contacting hair with a hair straightening/relaxing composition consisting of:
      (i) from about 0.1 to about 50% by weight of at least one weak non-hydroxide base selected from the group consisting of a monoethanolamine, an alkali metal phosphate, an alkali metal carbonate, an alkali metal carboxylate, ethylenediamine, quinoline, aniline, and pyridine; and
      (ii) a cosmetically acceptable medium and optionally an adjuvant, all weights based on the weight of the hair straightening/relaxing composition, this forming treated hair;
   (b) optionally, rinsing the hair straightening/relaxing composition from the treated hair;
   (c) contacting the treated hair with a non-volatile oil; and
   (d) smoothing the treated hair using a combination of heat and means for physically smoothing hair.
2. The process of claim 1 wherein (a)(i) is employed in an amount of from about 0.1 to about 30% by weight, based on the weight of the hair straightening/relaxing composition.
3. The process of claim 1 wherein (a)(i) is monoethanolamine.
4. The process of claim 1 wherein (a)(i) is chosen from an alkali metal phosphate, an alkali metal carbonate, and mixtures thereof.
5. The process of claim 1 wherein (a)(i) is chosen from sodium phosphate, potassium phosphate, and mixtures thereof.
6. The process of claim 1 wherein (a)(i) is sodium carbonate.
7. The process of claim 1 wherein (a) is performed for less than about 60 minutes.
8. The process of claim 1 wherein (a) is performed for less than about 20 minutes.
9. The process of claim 1 wherein the process is performed without the use of a barrier substance.
10. The process of claim 1 wherein (c) is chosen from plant, mineral, animal and synthetic oils.
11. The process of claim 1 wherein (a)(i) is employed in an amount of from about 0.2 to about 15% by weight, based on the weight of the hair straightening/relaxing composition.
12. The process of claim 1 wherein the heat employed in step (d) is at least about 50° C.

13. The process of claim 1 wherein the heat employed in step (d) is at least about 100° C.

14. The process of claim 1 wherein the means for physically smoothing hair is chosen from a brush and a comb.

15. The process of claim 1 wherein step (d) is performed using a hot/flat iron at a temperature of at least about 100° C.

16. The process of claim 1, wherein the weak non-hydroxide base is an alkali metal carbonate selected from the group consisting of sodium carbonate, potassium carbonate, sodium bicarbonate and potassium bicarbonate.

17. The process of claim 1, wherein the weak non-hydroxide base is an alkali metal carboxylate selected from the group consisting of sodium citrate, potassium citrate, sodium acetate and potassium acetate.

18. The process of claim 1, wherein the weak non-hydroxide base is selected from the group consisting of an ethylenediamine, quinoline, aniline, and pyridine.

19. The process of claim 1, wherein the cosmetically acceptable medium is water, an organic solvent, or a combination thereof.

20. The process of claim 1, wherein the adjuvant is selected from the group consisting of silicones, nonionic, anionic, cationic and amphoteric surfactants, ceramides, glycoceramides and pseudoceramides, vitamins and provitamins, waxes other than ceramides, glycoceramides and pseudoceramides, water-soluble and liposoluble, silicone-based and non-silicone-based sunscreens, nacreous agents and opacifiers, sequestering agents, plasticizers, solubilizers, acidifying agents, mineral and organic thickeners, antioxidants, hydroxy acids, penetrating agents, fragrances, conditioning agents, and preserving agents, and combinations thereof.

21. The process of claim 1, wherein the composition is in the form of a liquid, a cream or a gel.

22. The process of claim 20, wherein the adjuvant does not include a hydroxy acid.

\* \* \* \* \*